US012130286B2

(12) United States Patent
Forouzanfar et al.

(10) Patent No.: US 12,130,286 B2
(45) Date of Patent: Oct. 29, 2024

(54) BIOSENSORS FOR DETECTING BIOMARKERS AND METHODS OF FABRICATING AND USING THE SAME

(71) Applicants: Shahrzad Forouzanfar, Miami, FL (US); Iman Khakpour, Miami, FL (US); Nezih Pala, Miami, FL (US); Chunlei Wang, Miami, FL (US)

(72) Inventors: Shahrzad Forouzanfar, Miami, FL (US); Iman Khakpour, Miami, FL (US); Nezih Pala, Miami, FL (US); Chunlei Wang, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 17/806,109

(22) Filed: Jun. 9, 2022

(65) Prior Publication Data

US 2023/0400454 A1 Dec. 14, 2023

(51) Int. Cl.
| | | |
|---|---|---|
| *G01N 33/543* | (2006.01) | |
| *G01N 27/30* | (2006.01) | |
| *G01N 27/327* | (2006.01) | |
| *G01N 33/574* | (2006.01) | |

(52) U.S. Cl.
CPC ....... *G01N 33/5438* (2013.01); *G01N 27/308* (2013.01); *G01N 27/3276* (2013.01); *G01N 33/57484* (2013.01); *G01N 2333/49* (2013.01)

(58) Field of Classification Search
CPC ............. G01N 27/308; G01N 27/3276; G01N 2333/49; G01N 33/5438; G01N 33/57484
See application file for complete search history.

(56) References Cited

U.S. PATENT DOCUMENTS

| 11,034,584 B1 | 6/2021 | Baboukani et al. |
| 11,352,703 B2 | 6/2022 | Khakpour et al. |
| 2014/0057339 A1* | 2/2014 | Esfandyarpour ............... G01N 33/54313 435/287.2 |

FOREIGN PATENT DOCUMENTS

CN 108152349 A * 6/2018 ......... G01N 27/3278

OTHER PUBLICATIONS

Zhang et al., Biosensors and Bioelectronics, 2017, 89, 735-742. (Year: 2017).*
English Machine Translation of CN 108152349 (Year: 2018).*
Komarov et al., International Journal of Mechanical Engineering and Technology, 2018, 1420-1430 (Year: 2018).*
Tabasi et al., Biosensors and Bioelectronics, 2017, 95, 117-123 (Year: 2017).*
Allagui et al., Nature, Scientific report, 2016, 1-8 (Year: 2016).*

(Continued)

*Primary Examiner* — Gurpreet Kaur
(74) *Attorney, Agent, or Firm* — SALIWANCHIK, LLOYD & EISENSCHENK

(57) ABSTRACT

Biosensors capable of detecting certain biomarkers (e.g., platelet-derived growth factor-BB (PDGF-BB)), as well as methods of fabricating the same and methods of using the same, are provided. The biosensors can be disposable and/or label-free. Electrochemical bipolar exfoliation can be used to exfoliate, reduce, and deposit (in a single step) graphene nanosheets on a desired substrate (e.g., an electrode). Affinity aptamers can be immobilized on the graphene nanosheets disposed on the substrate.

12 Claims, 7 Drawing Sheets

(56) References Cited

OTHER PUBLICATIONS

Yesim Tugce Yaman et al., Peptide nanoparticles (PNPs) modified disposable platform for sensitive electrochemical cytosensing of DLD-1 cancer cells, Biosensors and Bioelectronics 104 (2018) 50-57, 8 pages.

Yang Wang et al., Label-free microfluidic paper-based electrochemical aptasensor for ultrasensitive and simultaneous multiplexed detection of cancer biomarkers, Biosensors and Bioelectronics 136 (2019) 84-90, 7 pages.

Sunsanita Carvajal et al., Disposable InkJet-Printed Electrochemical Platform for Detection of Clinically Relevant HER-2 Breast Cancer Biomarker, Biosens Bioelectron. May 1, 2018; 104: 158-162. doi:10.1016/j.bios.2018.01.003, 13 pages.

Fahmida Alam et al., Flexible and Linker-Free Enzymatic Sensors Based on Zinc Oxide Nanoflakes for Noninvasive L-Lactate Sensing in Sweat, IEEE Sensors Journal, vol. 20, No. 10, May 15, 2020, 8 pages.

* cited by examiner

| Electrode | Modification | Technique | Detection strategy | LoD | Linear range | Stability |
|---|---|---|---|---|---|---|
| GCE | Cu-MOFs/TpBD-COFs | DPV | Label-free | 0.034 pg mL$^{-1}$ | 0.0001–60 ng mL$^{-1}$ | N/A |
|  | HAP-NPs | SWV | Labeled: HAP-NPs | 50 fg mL$^{-1}$ | 0.1 pg mL$^{-1}$ to 10 ng mL$^{-1}$ | N/A |
| C-MEMS thin film | Oxygen plasma etching | CV | Label-free | 7 pM | 0.01–50 nM | 90.34% after 10 days |
|  |  | EIS |  | 1.9 pM | 0.005–50 nM |  |
| Au | AuNPs | SWV | Labeled: α-cyclodextrin | 0.52 nM | 0.52–1.52 nM | 96.4% after 7 days |
|  | Graphene doped with silver nanoclusters | EIS | Label-free | 26.5 fM | 32.3 fM to 1.61 pM | 96.7% after 10 days |
| SS | BPE:rGO | DPV | Label-free | 0.53 pM | 0.005–10 nM | 91.2% after 6 days |
| PET/Au |  |  |  | 0.65 pM | 0.0007–20 nM |  |

*a* GCE: glassy carbon electrode; Cu-MOFs: Cu-based metal-organic frameworks; TpBD-COFs: 1,3,5-triformylphloroglucinol (Tp), benzidine (BD) covalent organic frameworks (COFs); HAP-NPs: hydroxyapatite nanoparticles; SWV: square wave voltammetry; C-MEMS: carbon microelectromechanical systems; EIS: electrochemical impedance spectroscopy; AuNPs: gold nanoparticles.

FIG. 7

BIOSENSORS FOR DETECTING BIOMARKERS AND METHODS OF FABRICATING AND USING THE SAME

GOVERNMENT SUPPORT

This invention was made with government support under 1611088 awarded by the National Science Foundation. The government has certain rights in the invention.

BACKGROUND

Cancer is a significant cause of death, killing millions of people every year. Most cancers have a high fatality rate because cancer is diagnosed when it has significantly progressed and invaded many vital organs. The main reason for such a late diagnosis is that patients with cancer often have no physical symptoms at the early stages of the disease. Many cancer biomarkers associated with various cancer diseases have been discovered. Among the discovered cancer biomarkers, platelet-derived growth factor-BB (PDGF-BB) is known to have a potent role in the growth and metastasis of several solid malignant tumors, and its levels in the blood increase under the influence of cancer. PDGF-BB is involved in the development and lymphatic metastasis of various cancers, including breast, pancreatic, prostate, ovarian, and liver. There is a correlation of elevated levels of PDGF-BB in human serum with cancer, though there is no Food and Drug Administration (FDA) official report for healthy and cancerous levels of PDGF-BB in human blood.

BRIEF SUMMARY

Embodiments of the subject invention provide novel and advantageous biosensors capable of detecting certain biomarkers (e.g., platelet-derived growth factor-BB (PDGF-BB)), as well as methods of fabricating the same and methods of using the same. The biosensors can be disposable and/or label-free. Electrochemical bipolar exfoliation can be used to exfoliate, reduce, and deposit (e.g., in a single step) graphene nanosheets on desired substrates (e.g., an electrode such as a gold electrode). Affinity aptamers can be immobilized on the graphene nanosheets disposed on the substrate. The biosensors can have highly sensitive, selective, and stable sensing performance.

In an embodiment, a biosensor for detecting a biomarker can comprise: an electrode comprising a metal; reduced graphene oxide (rGO) disposed on the electrode; and a plurality of aptamers disposed on the rGO, the plurality of aptamers being configured to bind to the biomarker. The metal of the electrode can be, for example, gold (Au) and/or stainless steel (SS). The electrode can further comprise a substrate on which the metal is disposed, and the substrate can be, for example, a polymer (e.g., polyethylene terephthalate (PET)). The biomarker can be a cancer biomarker (e.g., PDGF-BB). The rGO can cover at least 60% (or at least 70%, at least 80%, at least 90%, at least 95%, or at least 99%) of an upper surface (i.e., the surface on which the aptamers are disposed) of the metal of the electrode. The biosensor can be label-free and/or disposable. The biosensor can have a lower limit of detection for the biomarker of less than 1 picomolar (pM) (e.g., less than 0.7 pM).

In another embodiment, a method of fabricating a biosensor for detecting a biomarker can comprise: providing a positive feeding electrode, a negative feeding electrode, and a graphite rod in water; applying a direct current (DC) voltage to the positive feeding electrode and the negative feeding electrode to perform a single-step exfoliation, reduction, and deposition of graphene nanosheets on the positive feeding electrode and the negative feeding electrode, the graphene nanosheets deposited on the negative feeding electrodes comprising rGO; removing the negative feeding electrode from the water; and immobilizing a plurality of aptamers on the rGO of the negative feeding electrode, the plurality of aptamers being configured to bind to the biomarker. The negative feeding electrode can comprise a metal (e.g., Au and/or SS). The negative feeding electrode can further comprise a substrate on which the metal is disposed, and the substrate can be, for example, a polymer (e.g., PET). The biomarker can be a cancer biomarker (e.g., PDGF-BB). The rGO can cover at least 60% (or at least 70%, at least 80%, at least 90%, at least 95%, or at least 99%) of an upper surface (i.e., the surface on which the aptamers are disposed) of the metal of the negative feeding electrode. The water can be, for example, deionized water (e.g., deionized water with no additives, such that the positive feeding electrode, the negative feeding electrode, and the graphite rod are disposed only in deionized water, with no additives included in the solution that is deionized water).

BRIEF DESCRIPTION OF DRAWINGS

FIG. 7 shows a table showing performance of different electrochemical PDGF-BB aptasensors.

DETAILED DESCRIPTION

Figures 1A, 1B, 1C, 1D:
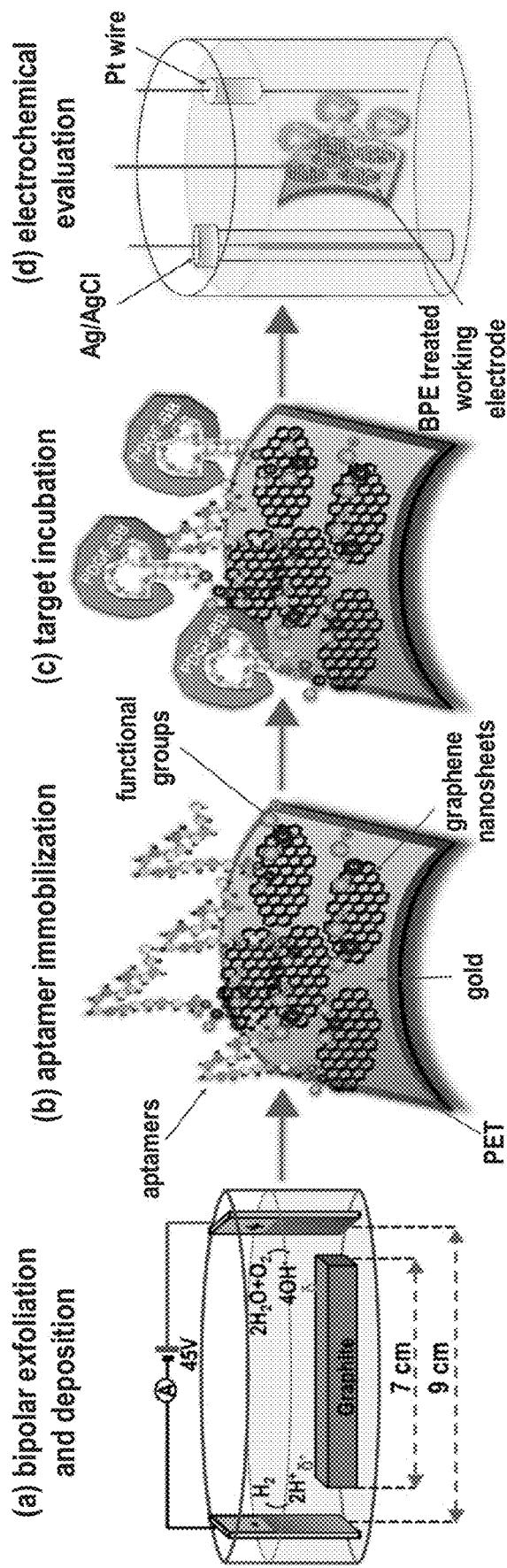
FIG. 1(a) shows a schematic view of a bipolar exfoliation cell, according to an embodiment of the subject invention.
FIG. 1(b) shows a schematic view of aptamer immobilization in the development of an aptasensor, according to an embodiment of the subject invention, using an electrode from FIG. 1(a). Though the materials are depicted as polyethylene terephthalate (PET) and gold, these are for demonstrative purposes only and should not be construed as limiting; other materials could be used.
FIG. 1(c) shows a schematic view of target incubation on the aptasensor of FIG. 1(b).
FIG. 1(d) shows a schematic view of a three-electrode electrochemical cell. Though a silver/silver chloride (Ag/AgCl) reference electrode and a platinum (Pt) wire counter electrode are depicted, these are for demonstrative purposes only and should not be construed as limiting; other materials could be used.

Bipolar electrochemistry is a versatile technique for exfoliation and selective deposition of various materials, including graphene nanosheets. Embodiments of the subject invention provide electrochemical biosensors capable of detecting certain biomarkers (e.g., platelet-derived growth factor-BB (PDGF-BB)), as well as methods of fabricating the same and methods of using the same. The biosensors can be disposable and/or label-free. Electrochemical bipolar exfoliation can be used to exfoliate, reduce, and deposit (e.g., in a single step) graphene nanosheets on desired substrates (e.g., an electrode such as a gold electrode). Affinity aptamers can be immobilized (e.g., directly immobilized (i.e., without mediator or linking layers)) on the graphene nanosheets disposed on the substrate. The biosensors can have highly sensitive, selective, and stable sensing performance. Embodiments provide highly repeatable and expandable fabrication procedures for point-of-care (POC) biosensors (e.g., disposable POC biosensors), which are useful for mass production and lab-on-chip applications. Electrochemical bipolar exfoliated graphene is not used in the related art for label-free detection of PDGF-BB cancer biomarkers. Embodiments of the subject invention can open new avenues for affordable POC cancer biomarker detection, which can be used to detect PDGF-BB and other cancer biomarkers detectable from human blood.

Embodiments of the subject invention provide highly sensitive aptasensors based on bipolar electrochemical exfoliated graphene, and the aptasensors can be disposable (i.e., intended for a single use before being disposed of) and/or label-free aptasensor. The bipolar electrochemical exfoliation enables simultaneous exfoliation, reduction, and deposition of graphene nanosheets on the electrodes. The aptasensor can have highly selective performance with a high stability (e.g., of greater than 90% (e.g., 91.2%) after six days). Bipolar electrochemistry (BPE) is a simple yet efficient technique that provides high-quality graphene for biosensing applications. In view of the simplicity and efficiency of the used BPE technique, feasible and affordable lab-on-chip and POC cancer diagnosis technologies can be obtained.

Embodiments of the subject invention provide a broad range of detection that covers the healthy range of PDGF-BB concentration as well as the concentration in various cancers. This wide range of detection enables the biosensor to be used both as risk indicators of cancer and for monitoring the effect of applied therapies. Further, the essence of label-free detection is based on minimizing the efforts of modification of the samples before testing; hence, the biosensor can be used for continuous monitoring of cancer patients.

Label-free aptasensors of embodiments of the subject invention can be used as POC biosensors for detecting various cancers due to their selectivity, sensitivity, and lower cost of production and operation. A highly sensitive aptasensor can include at least one electrode (e.g., gold-covered electrode(s) such as gold (Au)-covered polyethylene terephthalate (PET) electrode(s) (PET/Au)) having bipolar exfoliated graphene disposed thereon (e.g., covering or mostly covering (e.g., >60% coverage, >70% coverage, >80% coverage, or >90% coverage) at least one surface of the electrode(s)). Bipolar electrochemical exfoliation enables simultaneous exfoliation, reduction, and deposition of graphene nanosheets on electrodes. BPE graphene deposited on the negative feeding electrode (i.e., reduced graphene oxide) can possess better electrochemical properties for aptasensing. An aptasensor based on BPE graphene deposited on at least one electrode (e.g., a negative feeding electrode, such as an Au or PET/Au electrode) exhibits a highly sensitive response and can have a low limit of detection (e.g., less than 1 picomolar (pM), such as 0.65 pM (S/N=3)). The aptasensor can show highly selective performance with a stability of at least 90% (e.g., 91.2%) after at least five days (e.g., after six days).

In an embodiment, before Au deposition, PET sheets can be washed with isopropyl alcohol (IPA) and/or deionized water (DIW) (e.g., for 15 minutes (min) or about 15 min) using an ultrasonic bath. Subsequently, the PET sheets can be dried up (e.g., using nitrogen gas ($N_2$)). A thin Au layer (e.g., a 60 nanometer (nm) Au layer) can be deposited using e-beam evaporation on PET substrates with a thin adhesive titanium layer (e.g., 20 nm). Stainless steel (SS) sheets and the PET/Au sheets can be thoroughly washed with IPA and/or DIW (e.g., using $N_2$ gas) before BPE deposition. In a particular embodiment, two SS or PET/Au electrodes (e.g., 2 square centimeters ($cm^2$) by 1 $cm^2$) placed 9 centimeters (cm) or about 9 cm apart in DIW can be used as the feeding electrodes for the bipolar electrochemical setup. For BPE deposition, a direct current (DC) voltage (e.g., of 45 Volts (V)) can be applied across the feeding electrodes for a predetermined period of time (e.g., 24 hours or about 24 hours), which can result in an electric field (e.g., an apparent electric field of 5 Volts per centimeter (V/cm)). After BPE deposition, the electrodes can be washed (e.g., with DIW) and dried (e.g., under $N_2$ gas) and/or stored in gas-tight containers before further use. One or more aptamer stock solutions can be prepared. The diluted stocks can be prepared in a buffer (e.g., a tris-ethylenediaminetetraacetic acid (TE) buffer, such as one with a concentration of 0.1 molar (M)), giving a final volume of, for example, 10 microliters (μl) or about 10 μl. Before immobilizing aptamers, 5 μl of 20 milligram per milliliter (mg/ml) 1-ethyl-3-(3-dimethylaminopropyl) carbodiimide hydrochloride linker (EDC) and 10 μl of 20 mg/ml N-hydroxysuccinimide linker (NHS) may be added to the aptamer solution with the desired concentration ranging from, for example, 5 micromolar (μM) to 50 μM. The aptamer solution can be incubated for, e.g., 30 minutes (or about 30 minutes) at, e.g., room temperature. This step can be useful for activating the amino linker tags of the aptamers. The prepared aptamer solution can be deposited on the BPE-treated electrode surface(s), which may be followed by an optional incubation (e.g., for 24 hours or about 24 hours at, for example, room temperature). After incubation, electrodes can be washed thoroughly (e.g., in DIW) to wash any unattached aptamers. In order to quench blank areas of the BPE-treated electrodes, a solution (e.g., 50 μl of an aqueous solution of 0.1 M phosphate-buffered saline (PBS)+1% (v:v) Tween-20) can be deposited on the electrodes followed by an optional incubation (e.g., for 10 minutes or about 10 minutes). The aptamer immobilized electrodes can be designated as SS/GO$_{Apt}$ (SS electrode with graphene oxide (GO) and an immobilized aptamer), SS/rGO$_{Apt}$ (SS electrode with reduced graphene oxide (rGO) and an immobilized aptamer), PET/Au/rGO$_{Apt}$ (PET/Au electrode with rGO and an immobilized aptamer). The electrode(s) can be washed (e.g., with DIW for 5 minutes or about 5 minutes) and can optionally be stored in a solution (e.g., a buffer solution such as 0.1 M TE buffer) at a reduced temperature (e.g., in a refrigerator (less than 5° C., such as 4° C. or about 4° C.) when not in use.

The significant role of PDGF-BB in development and metastasis of different cancers emphasizes the importance of developing point-of-care (POC) biosensors to detect PDGF-BB biomarker. PDGF-BB POC biosensors can be an immense help for the early diagnosis of many cancers associated with solid tumors such as breast, brain, prostate, ovarian, and lung cancers.

The price of sensing units is one of the major concerns in developing feasible POC biosensors. Sensing units of embodiments of the subject invention can provide accurate sensing and be cheap enough to rationalize installment for in-site applications. Combining label-free detection with economically efficient manufacturing techniques can be a promising option for developing versatile sensing systems to detect and monitor different bio-targets, including PDGF-BB. Various substrates such as paper, polymers (e.g., polyethylene terephthalate), and screen-printed carbon electrodes can be used for developing disposable biosensors.

Further, the emergence of the COVID-19 pandemic in early 2020 highlighted the importance of fast, reliable, and affordable POC biosensors suitable for the detection of various biotargets (e.g., SARS-CoV-2). The integration of artificial intelligence (AI) and internet of things (IoT) with POC pathogen biosensors means that POC biosensors can be effectively used for performing personalized diagnostics under desired conditions and at desired locations, helping the management of the epidemic in an economic and timely manner. Hence, integration of AI and IoT with cancer biomarker POC biosensors can be an effective strategy to make a significant impact on the diagnosis and management of cancer.

Graphene has large surface area, high thermal conductivity and charge mobility, wide electrochemical window, and unconventional superconductivity, making this material a good candidate for the development of biosensors. Conventional application of graphene for biosensors includes synthesis of graphene with wet chemical processes (e.g., Hummers) or electrochemical approaches. Wet chemical synthesis requires harsh oxidizing agents such as $KMnO_4$, $NaNO_3$, and $KClO_3$ in strong acidic agents such as hydrohalic acid and hydrazine. The application of harsh chemicals can be limited using electrochemical approaches; however, there could be non-desired functional groups and basal plane damage during the anodic exfoliation. Also, commercially available graphene has low graphene content (less than 10% in most products and typically not more than 50%), which illustrates why commercial graphene-based devices are not commonly available yet. Nonetheless, conventional methods for synthesis and deposition of GO and rGO cannot simultaneously exfoliate, reduce, and deposit GO and rGO in an environmentally friendly fashion. Such a combination can be achieved via the application of bipolar electrochemistry. In addition, bipolar exfoliated rGO has vertically aligned morphology, which can eliminate the necessity of using spacers such as carbon nanotubes to prevent or inhibit the aggregation of graphene nano-flakes.

Embodiments of the subject invention provide the novel application of bipolar exfoliation of graphene for disposable label-free PDGF-BB aptasensors. Application of bipolar exfoliated (BPE) graphene for biosensors is not done in the related art. The bipolar exfoliation methods of embodiments of the subject invention include a direct single step of exfoliation, deposition, and reduction of graphene utilizing a graphite rod in water (e.g., deionized water (DIW)). The process of bipolar exfoliation includes applying a constant electric field between two conductive feeder electrodes, which aggregates in opposite polarizations of the graphite rods. Consequently, if the apparent potential difference between opposite ends of the rod is sufficient (i.e., >1.5 Volts (V)), simultaneous faradaic reactions of reduction at the cathodic pole and oxidation at the anodic pole can occur. BPE can be used various applications due to the simplicity of the setup and lower cost of the process.

FIG. 1($a$) shows a bipolar exfoliation cell, according to an embodiment of the subject invention. Referring to FIG. 1($a$), the cell can be used for a direct, single-step exfoliation, reduction, and deposition of graphene nanosheets on electrodes (e.g., SS and/or PET/Au electrodes). With respect to the bipolar mechanism, a voltage (e.g., a direct current voltage, such as 45 V or about 45 V DC) can be applied through the feeding electrodes (e.g., 2 centimeter (cm)×2 cm feeding electrodes) spaced apart from each other by a predetermined distance (e.g., 9 cm) to induce an electric field of (e.g., 5 Volts per centimeter (V/cm)). The resistivity of water (e.g., DIW) used for bipolar exfoliation can be, for example, 17 megaOhms (MΩ) or about 17 MΩ. During bipolar exfoliation, two half-reactions of water electrolysis happen at the feeding electrodes: (1) reduction of two water molecules to one gaseous hydrogen molecules ($2H^+ + 2e^- \rightarrow H_2$) and hydroxyl ions ($OH^-$) at the cathode; and (2) oxidation of hydroxyl ions ($OH^-$) to oxygen gas and water molecules ($4OH^- \rightarrow 2H_2O + O_2 + 4e^-$) at the anode (see also, e.g.; Allagui et al., Scientific reports, 6, 21282, 2016; Khakpour et al., ACS Applied Energy Materials, 2, 4813, 2019; Suter et al., Advanced Materials, 32, 2003213, 2020; and Ashraf et al., ChemElectroChem, 4, 2084, 2017; all four of which are hereby incorporated by reference herein in their entireties). Further, assuming that the potential drop is negligible at the electrodes and linear in the solution, the electric field induces a sufficient potential difference (i.e., >1.5 V) between two ends of the graphite rod to stimulate faradic reactions at the side surfaces of the graphite rod. This potential difference yields in the oxidation of graphite into GO at the anodic pole of the graphite rod (indicated as $\delta^+$ in FIG. 1($a$)). Though FIG. 1($a$) lists specific distances and voltage values, these are for demonstrative purposes only and should not be construed as limiting.

Prior to immobilizing aptamers, each electrode can be examined (e.g., with SEM) to confirm the uniform (or nearly uniform) deposition of rGO or GO on the electrodes. Next, the amino-modified PDGF-BB affinity aptamers can be immobilized on electrodes (e.g., SS and/or PET/Au electrodes) modified with BPE-graphene. This is illustrated in FIG. 1($b$). The aptasensors can be incubated with a predetermined desired PDGF-BB concentration at one or more predetermined temperatures (e.g., ranging from 20° C. to 50° C.) for a predetermined amount of time (e.g., between 10 minutes and 150 minutes); this is depicted in FIG. 1($c$). An optimum incubation temperature in certain cases can be 35° C. (or about 35° C.), with an associated optimum reaction time for target molecules to bind with aptamers of 40 minutes (or about 40 minutes). A three-electrode setup illustrated in FIG. 1($d$) can be used for differential pulse voltammetry (DPV) and/or cyclic voltammetry (CV) evaluations of the electrodes. Aqueous electrolytes can be used for electrochemical analysis (e.g., 5 mL aqueous electrolytes of 0.1 molar (M) PBS, 5 millimolar (mM) $k_3Fe(CN)_6$, and different KCl concentrations in the range of 50 mM to 1 M can be utilized for electrochemical analysis).

In an embodiment, a method of detecting a biomarker can comprise: providing a biosensor as disclosed herein; exposing the biosensor to a solution suspected of containing the biomarker; and analyzing the biosensor to determine the quantity of biomarker (if any) that has bound to aptamers of the biosensor.

Biosensors of embodiments of the subject invention can be disposable and/or wearable. The simplicity of electrochemical bipolar exfoliation of graphene and the process's environmental friendliness can be harnessed for various applications, including but not limited to integration with carbon-microelectromechanical systems (C-MEMS) technology for biosensing, biofuel cell, and implantable electrodes. Further, the integration of BPE-graphene on C-MEMS flexible substrates can be used for wearable biosensors.

Certain aspects of U.S. Pat. Nos. 11,034,584 and 11,352,703 are relevant to embodiments of the subject invention, and both of these documents are hereby incorporated by reference herein in their entireties.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

When ranges are used herein, such as for dose ranges, combinations and subcombinations of ranges (e.g., subranges within the disclosed range), specific embodiments therein are intended to be explicitly included. When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

Materials and Methods

A three-electrode setup as shown in FIG. 1(d) was used for DPV and CV evaluations of the electrodes. 5 mL aqueous electrolytes of 0.1 M PBS, 5 mM $k_3Fe(CN)_6$, and different KCl concentrations in the range of 50 mM to 1 M were utilized for electrochemical analysis.

Electrochemical and FTIR characterizations were conducted on four different BPE-treated SS electrodes referred to as SS/GO, SS/rGO, SS/GO$_{Apt}$, and SS/rGO$_{Apt}$, which represent the samples of GO deposited on SS electrode (i.e., positive feeding electrode), rGO on deposited SS electrode (i.e., negative feeding electrode), aptamer immobilized on SS/GO electrode, and aptamer immobilized on SS/rGO electrode, respectively. The aptamer concentration of 15 micromolar (μM) was used to fabricate SS/GO$_{Apt}$, SS/rGO$_{Apt}$, and PET/Au/rGO$_{Apt}$ electrodes in the following examples except for PET/Au/rGO$_{Apt}$ electrodes prepared for defining the optimum concentration of aptamer. The optimum aptamer concentration of 10 μM was utilized to fabricate PET/Au/rGO$_{Apt}$ electrodes in example 4. All BPE-treated electrodes had an effective area of 0.5 square centimeters (cm$^2$) confined via bee's wax to minimize side reactions.

The BPE-graphene was deposited on SS for comparative analysis, including studying the electrochemical characteristics of BPE-graphene and its compatibility for aptamer immobilization. The analysis confirmed that the BPE-rGO deposited on the cathodic (i.e., negative) feeding electrode is highly suitable for aptasensing applications. Thus, the gold-covered polyethylene terephthalate electrodes (designated as PET/Au) were used as negative feeding electrodes. The amino-terminated PDGF-BB affinity aptamers were covalently immobilized on BPE-graphene deposited on SS and PET/Au electrodes. The BPE-graphene crystal structure and its morphology were studied via transmission electron microscopy (TEM) and scanning electron microscope (SEM), respectively. The characteristics of the fabricated BPE-based aptasensors were studied using Fourier-transform infrared spectroscopy (FTIR). Electrochemical and sensing performance analyses were conducted using differential pulse voltammetry (DPV) and cyclic voltammetry (CV). The results revealed that the bipolar exfoliation provides high quality rGO with promising characteristics suitable for aptasensors. In addition, the BPE technique was proven to be both versatile and amenable to mass production, thus making it an excellent technique for various biotechnology applications, including but not limited to (disposable) cancer aptasensors and (wearable) POC microdevices.

The PDGF-BB binding aptamer (ssDNA, amino linker-5'-$C_6$-CAG GCT ACG GCA CGT AGA GCA TCA CCA TGA TCC TG-3') was purchased in high-performance liquid chromatography (HPLC) purification from ThermoFisher Scientific, USA. Tri s-ethylenediaminetetraacetic acid (TE) buffer, ethanol, acetone, phosphate-buffered saline (1M and pH 8) (PBS), 1-ethyl-3-(3-dimethylaminopropyl) carbodiimide hydrochloride linker (EDC), N-hydroxysuccinimide linker (NETS), hydrochloric acid (HCl), Polyoxyethylene (20) sorbitan monolaurate (Tween-20), KCl, and $k_3Fe(CN)_6$ were purchased from ThermoFisher Scientific, USA. Trehalose, bovine serum albumin (BSA), platelet-derived growth factor-AA, AB, and BB were purchased from Sigma Aldrich, USA. NANO™. SU-8 25 negative photoresist was purchased from Microchem., USA. Graphite rods (3 cm in length and 6.15 mm in diameter, Ultra "F" Purity 99.9995%) were purchased from Fisher Scientific, USA. The 316 stainless steel (SS) electrodes were purchased from Maudlin Inc., USA. All chemicals were analytical grade. Milli-Q (Sigma Aldrich, USA) deionized water was used in this study.

A Bio-Logic versatile multichannel potentiostat (VMP3) was used for the electrochemical analysis. JEOL SEM 6330 and Philips CM-200 FEG TEM were used to obtain the SEM and TEM images of the deposited materials, respectively. Agilent Technologies N6705A DC Power Analyzer was used for applying a DC voltage of 45 V across the feeding electrodes. An Ag/AgCl (KCl saturated) and Pt wire were used as reference electrode and working electrodes in all electrochemical measurements, respectively. A 713 Metrohm pH meter was used for measuring the pH of electrolytes. JASCO FTIR 4100 was used to conduct FTIR analysis.

Prior to aptamer immobilization, the BPE-treated SS and PET/Au electrodes were washed with phosphate buffered saline (PBS) and DIW. The stock solution of binding aptamers was diluted to the desired concentration in aqueous solution of a 0.1 M TE buffer in the final volume of 20 microliters (μl). Next, 20 μL of 20 milligram per milliliter (mg/ml) NHS and 10 μl of 20 mg/ml EDC were added to the aptamer solution and incubated at 25° C. for 30 minutes. Next, the BPE-treated electrodes were dipped in a small, sealed container and incubated overnight at 25° C. Following the incubation, the electrodes were washed completely in DIW to remove any unattached binding aptamers. Next, the electrodes with immobilized aptamer were dipped in an aqueous solution of 1% (v:v) Tween-20+0.1 M PBS to block the blank areas of the aptasensors.

The CV measurements were recorded at a voltage window of −0.8 V to 0.4 V versus the reference electrode with scan rates of 10 millivolts per second (mV/s)-100 mV/s and cycle repeating of n=20. DPV measurements were recorded at a voltage range of 0.2 V to 0.9 V (vs Ag/AgCl) for SS based electrodes and −0.05 V to 0.5 V (vs Ag/AgCl) for PET/Au based electrodes with a pulse height of 200 mV and pulse width of 100 milliseconds (ms) with n=10 number of repetitions. The electrolyte pH was attuned using HCl to attain electrolytes with a pH of 8-5.5.

Example 1—Material Characterization of BPE Treated Electrodes

Figures 2A, 2B, 2C:
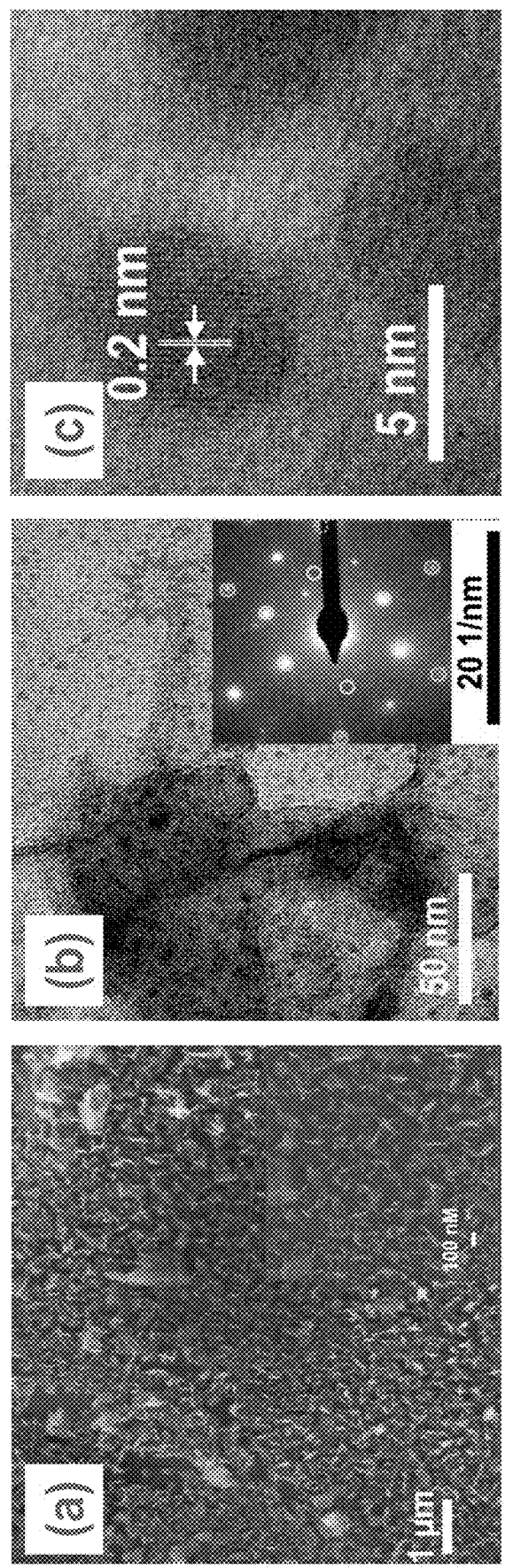
FIG. 2(a) shows scanning electron microscope (SEM) images of bipolar exfoliated (BPE) reduced graphene oxide (rGO) (BPE-rGO) deposited on a negative feeding electrode. The scale bar is 1 micrometer (μm) for the main image, and the scale bar is 100 nanometers (nm) for the inset image).
FIG. 2(b) shows a transmission electron microscope (TEM) image and a selected area electron diffraction (SAED) image (inset) of deposited BPE-rGO. The scale bar on the TEM image is 50 nm and on the SAED image is 20 1/nm.
FIG. 2(c) shows a high resolution transmission electron microscope (HRTEM) image of BPE-rGO. The scale bar is 5 nm, and the highlighted portion is 0.2 nm wide.

FIG. 2(a) shows a scanning electron microscope (SEM) image of BPE-rGO deposited on SS electrodes after 24 hours of deposition. The SEM image of rGO deposited on negative feeding electrodes plainly show a porous morphology with vertically aligned structures with a pore size of approximately 100 nanometers (nm). This porous morphology is highly suitable for various applications, including electrochemical biosensors and energy storage microdevices. On the other hand, GO deposited on positive feeding electrodes have bulky plane structures with cracks implying restacking of GO during the deposition stage.

FIG. 2(b) shows a transmission electron microscope (TEM) and selected area electron diffraction (SAED) image (inset) of BPE-rGO deposited on the TEM mesh. The TEM image shows that thin sheets of rGO (with overlaps or folds) with a span of approximately 400 nm are formed. Single crystalline SAED patterns confirm that the low defected graphene sheets are formed during the bipolar exfoliation. Only a few diffraction spots beside the spots related to the crystal are formed, and no superlattice arrays are identified in the deposited graphene. Therefore, it can be concluded that the BPE-rGO is reduced and has high purity.

Also, when the intensity of spots diffracted from $\langle 2\bar{1}\bar{1}0 \rangle$ planes is higher than the intensity of spots diffracted from $\langle 1\bar{1}00 \rangle$ planes, there is more than one layer stacked in the graphene material. It can be seen in the SAED pattern of TEM image of FIG. 2(b) that spots diffracted from $\langle 2\bar{1}\bar{1}0 \rangle$ planes (marked with the circles around the outside of the inset image) have lower intensity than spots diffracted from $\langle 1\bar{1}00 \rangle$ planes (marked with circles closer to the center of the inset image). The difference in the intensity of spots diffracted from $\langle 2\bar{1}\bar{1}0 \rangle$ planes and $\langle 1\bar{1}00 \rangle$ planes suggest the graphene deposited on negative feeding electrode is most probably single-layer graphene. The interplanar spacing (also known as d-spacing) of 0.2 nm is measurable from the high-resolution TEM (HRTEM) image presented in FIG. 2(c), in which the measured interplanar spacing is smaller than the typical value of GO.

Figure 3:
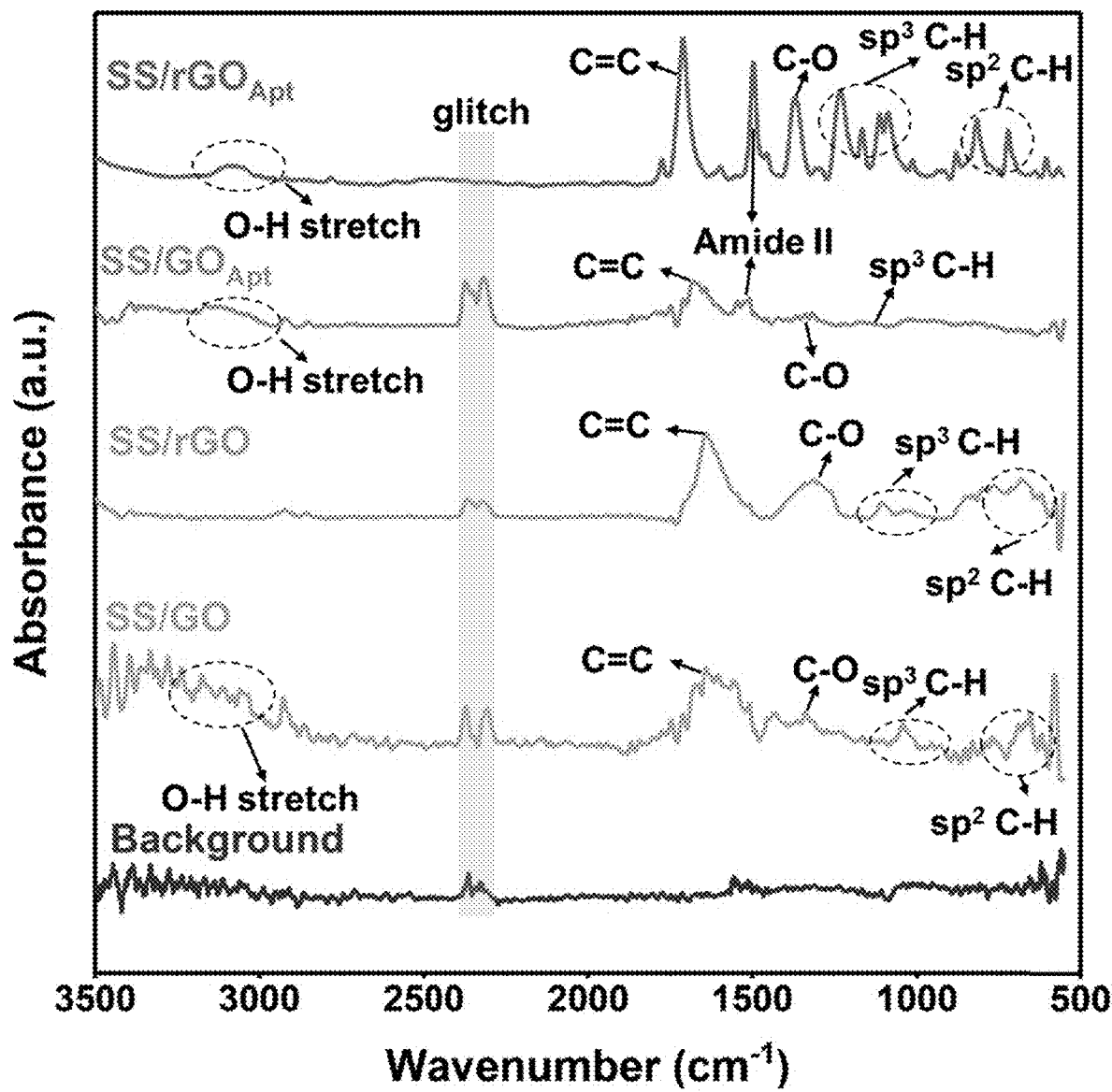
FIG. 3 is a plot of Fourier-transform infrared spectroscopy (FTIR) spectra for stainless steel (SS)/graphene oxide (GO) (SS/GO), SS/rGO, SS/GO$_{Apt}$ (SS/GO with aptamer immobilized thereon), and SS/rGO$_{Apt}$ (SS/rGO with aptamer immobilized thereon) electrodes.

The FTIR characterization was used to analyze the spectral data of the BPE-rGO and BPE-GO samples deposited on SS electrodes, including the formation of amide biding after aptamer immobilization. The FTIR spectra of background, SS/GO, SS/rGO, SS/GO$_{Apt}$, and SS/rGO$_{Apt}$ are shown in FIG. 3. Three samples of SS/GO, SS/GO$_{Apt}$, and SS/rGO$_{Apt}$ showed a broad peak between 2800-3200 cm$^{-1}$, which is ascribed to O—H stretching. The noteworthy peaks for all samples were identified at 1430 and 1600 cm$^{-1}$, ascribed to C—O bending and aromatic C≡C stretching, respectively. Also, all the samples showed peaks at 1100-1300 cm$^{-1}$, which are attributed to sp$^3$ C—H bending.

The FTIR spectrum for SS/GO$_{Apt}$ and SS/rGO$_{Apt}$ confirms a peak at 1571 cm$^{-1}$, associated with amide II band, representing covalent bonding of PDGF-BB aptamers with BPE-graphene. The FTIR results confirm that the locally formed carboxyl groups on the graphene surfaces can be used directly to immobilize the amino-terminated biorecognizers agents. The immobilization efficiency can also be improved using oxygen-plasma etching to increase the percentages of carboxyl groups on the surface of the BPE-graphene.

Example 2—Electrochemical Analysis of BPE-Graphene Samples

Electrochemical analysis of BPE-graphene based aptasensors in different stages of development was performed. The analysis intended to compare the different electrochemical properties of BPE-graphene deposited on negative and positive SS electrodes. Two hypotheses for comparative analysis of the BPE-based aptasensors were considered: first, the electrodes based on BPE-rGO exhibit better electrochemical performance than BPE-GO; second, trapped target molecules (i.e., the formation of target-aptamer complex) elevate the charge-transfer resistance by blocking redox species pass to the aptasensor electrode, which can be traced as decreasing current measured via the DPV method. A sample of 100 picomolar (pM) PDGF-BB (designated as T) was used as a target sample for electrochemical analysis purposes.

Figures 4A, 4B, 4C, 4D, 4E, 4F:
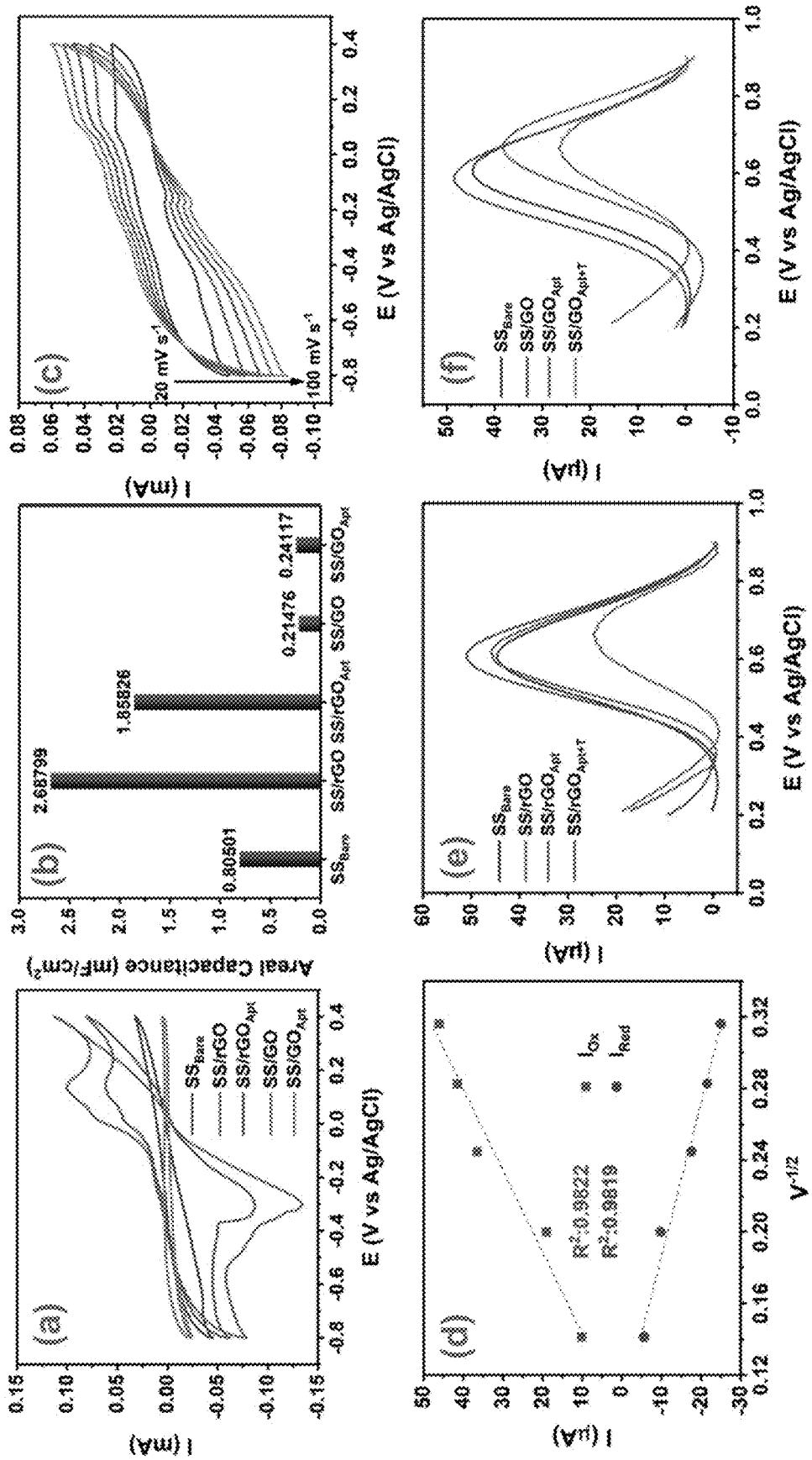
FIG. 4(a) is a plot of current (in milliamps (mA)) versus voltage (in Volts (V) versus silver/silver chloride (Ag/AgCl)) showing the CV plots (at 40 millivolts per second (mV/s)) of bare SS and BPE-graphene deposited on SS electrodes before and after aptamer immobilization.
FIG. 4(b) shows a bar chart of the areal capacitance (in milliFarads per square centimeter (mF/cm$_2$) calculated from the CV plots in FIG. 4(a).
FIG. 4(c) shows a plot of current (in mA) versus voltage (in V versus Ag/AgCl) showing the CV plots of the SS/rGO electrode at different scan rates in the range of 10 mV/s-100 mV/s.
FIG. 4(d) shows a plot of current (in microamps (μA)) versus the square root of scan rates showing calibration curves for oxidation (the curve with the higher values, $R^2$ of 0.9822) and reduction (curve with the lower values, $R^2$ of 0.9819).
FIG. 4(e) shows a plot of current (in μA) versus voltage (in V versus Ag/AgCl) showing the differential pulse voltammetry (DPV) plots of BPE-based aptasensors based on graphene deposited on the negative feeding electrode at various development stages and the sensing responses of the aptasensors to 100 picomolar (pM) platelet-derived growth factor-BB (PDGF-BB). The curve with the highest I value at 0.6 V is for SS/rGO$_{Apt}$; the curve with the second-highest I value at 0.6 V is for SS/rGO; the curve with the third-highest I value at 0.6 V is for SS$_{Bare}$; and the curve with the lowest I value at 0.6 V is for SS/rGO$_{Apt+T}$ (aptamer immobilized and target present).
FIG. 4(f) shows a plot of current (in μA) versus voltage (in V versus Ag/AgCl) showing the DPV plots of BPE-based aptasensors based on graphene deposited on the positive feeding electrode at various development stages and the sensing responses of the aptasensors to 100 pM PDGF-BB. The curve with the highest I value at 0.6 V is for SS/rGO$_{Apt}$; the curve with the second-highest I value at 0.6 V is for SS/rGO; the curve with the third-highest I value at 0.6 V is for SS$_{Bare}$; and the curve with the lowest I value at 0.6 V is for SS/rGO$_{Apt+T}$.

FIG. 4(a) shows CV curves measured for bare SS electrodes, four samples of BPE treated electrodes, and subsequent aptasensors. The CV curve of BPE-graphene deposited on the negative feeding electrode (i.e., SS/rGO) shows the highest peak currents and the largest CV curve area. The areal capacitances were calculated from CV curves using equation 1:

$$C = \frac{1}{2As\Delta V} \int IdV \quad (1)$$

where $\Delta V$ is the voltage window, s is scan rate, A is the electrode area, V is the voltage, and I is current. The calculated areal capacitances are given in FIG. 4(b). The SS/rGO electrode has the highest capacitance value with the areal capacitance of 2.69 milliFarad per square centimeter (mF/cm$^2$), while the SS/GO electrode has the lowest capacitance with a value of 0.24 mF/cm$^2$. Immobilizing aptamers decreased the areal capacitance of SS/rGO electrodes to a value of 1.86 mF/cm$^2$. This decrease is most probably because of partial replacement of double-layer with immobilized aptamers. The areal capacitance of SS/GO$_{Apt}$ is very similar to that of SS/GO with a value of 0.24 mF/cm$^2$, which can be explained by the low loading of immobilized aptamers on the surface of GO due to the limited active area of GO.

In order to estimate the electrochemically active area of BPE-rGO and BPE-GO using the Randles-Sevcik equation, the correlation of CV peak currents and the square root of scan rate were studied to confirm the occurrence of diffused-controlled process. The peak currents of CV measurement conducted on SS/rGO and SS/GO proportionally increased with the increase of scan rates at the scan rates of 10-100 millivolts per second (mV/s) (CV curves are given in FIG. 4(c)). The CV peak currents of SS/rGO linearly increased proportionally to the increase of scan rates' square root (FIG. 4(d)) with correlation coefficient (R$^2$) of 0.9819 and 0.9822 for reduction peak currents and oxidation peak currents, respectively. Similarly, the linear dependence of reduction and oxidation peak currents of SS/GO had R$^2$ of 0.9723 and 0.9891 for reduction and oxidation peak currents, respectively. Having the confirmation of diffused-controlled process occurrence, the active surface area of the BPE-rGO and BPE-GO samples were calculated using the Randles-Sevcik equation at room temperature (T=295 K) (equation 2).

$$I_P = (2.69 \times 10^5) n^{3/2} ACD^{1/2} v^{1/2} \quad (2)$$

where v is the scan rate (V/s), D is the diffusion coefficient of 5 mM Fe(CN)$_6^{-3/-4}$ (7.6×10$^{-6}$ cm$^2$ s$^{-1}$), C is the concentration of Fe(CN)$_6^{-3/-4}$ (5 mol/cm$^3$), n is electron transfer number (n=1), and A is active surface area (cm$^2$). For the Fe(CN)$_6^{-3/-4}$ redox couple, the active surface area of SS/rGO was calculated as 3.92×10$^{-5}$ cm$^2$, and the active surface area of SS/GO was calculated as 1.75×10$^{-5}$ cm$^2$. The calculated active area values show the BPE-rGO has a higher active area than the BPE-GO, which is in agreement with morphological analysis obtained from SEM images. Thus, the CV analysis, including areal capacitance and active area calculations, confirms the first hypothesis regarding better electrochemical properties of BPE-graphene deposited on the negative feeding electrode.

The DPV responses of BPE-rGO and BPE-GO aptasensors at different development stages are given in FIG. 4(e) and FIG. 4(f), respectively. The DPV response of SS/rGO shows a similar peak current to SS$_{Bare}$ (i.e., SS electrode without any modifications) with values of 45.8 microamps (µA) and 44.6 µA for SS/rGO and SS$_{Bare}$, respectively. These responses suggest a good electrochemical conductivity of deposited rGO on the SS electrode. However, the DPV response of SS/GO shows a decrease in peak current with a value of 37.9 µA, which is most probably because of the structure of GO and the functional groups covering the surface of SS/GO. The DPV response of SS/rGO$_{Apt}$ and SS/GO$_{Apt}$ show increased peak currents with a value of 51

µA and 48.4 µA, respectively. The increase in peak currents after aptamer immobilization can be explained by the engagement of negatively charged carboxylate groups in covalent immobilization of aptamers and extinguished remaining functional groups by Tween-20 quencher (see also, Forouzanfar et al., Biosensors and Bioelectronics, 170, 112598, 2020; which is hereby incorporated by reference herein in its entirety). The SS/rGO$_{Apt}$ and SS/GO$_{Apt}$ electrodes incubated with target molecules (i.e., SS/rGO$_{Apt+T}$ and SS/GO$_{Apt+T}$) have considerably lower peak currents with values of 24 µA for SS/rGO$_{Apt+T}$ and 26.5 µA for SS/GO$_{Apt+T}$, respectively. The decrease in peak currents is due to the isolative properties of the PDGF-BB oncoproteins, which decreases the pass of the redox species to the SS/rGO$_{Apt}$ and SS/GO$_{Apt}$ electrodes. Therefore, the DPV characterization of BPE-graphene-covered electrodes confirmed successful entrapment of PDGF-BB oncoproteins on the surfaces of the envisioned aptasensors and that seizing the target proteins decreases the peak current.

Example 3—Parameter Optimization and Comparison of Aptasensors Based on rGO and GO The effects of five parameters on responses of BPE-graphene based aptasensors were analyzed, including reaction-time, the temperature of incubation, pH of the electrolyte, concentration of supporting salt (i.e., KCl), and binding aptamer concentration. Among the analyzed parameters, the effect of aptamer concentration was studied explicitly for PET/Au-based aptasensors because the other four parameters are predominantly dependent on the DNA structures of the aptamers.

Figures 5A, 5B, 5C, 5D, 5E, 5F:
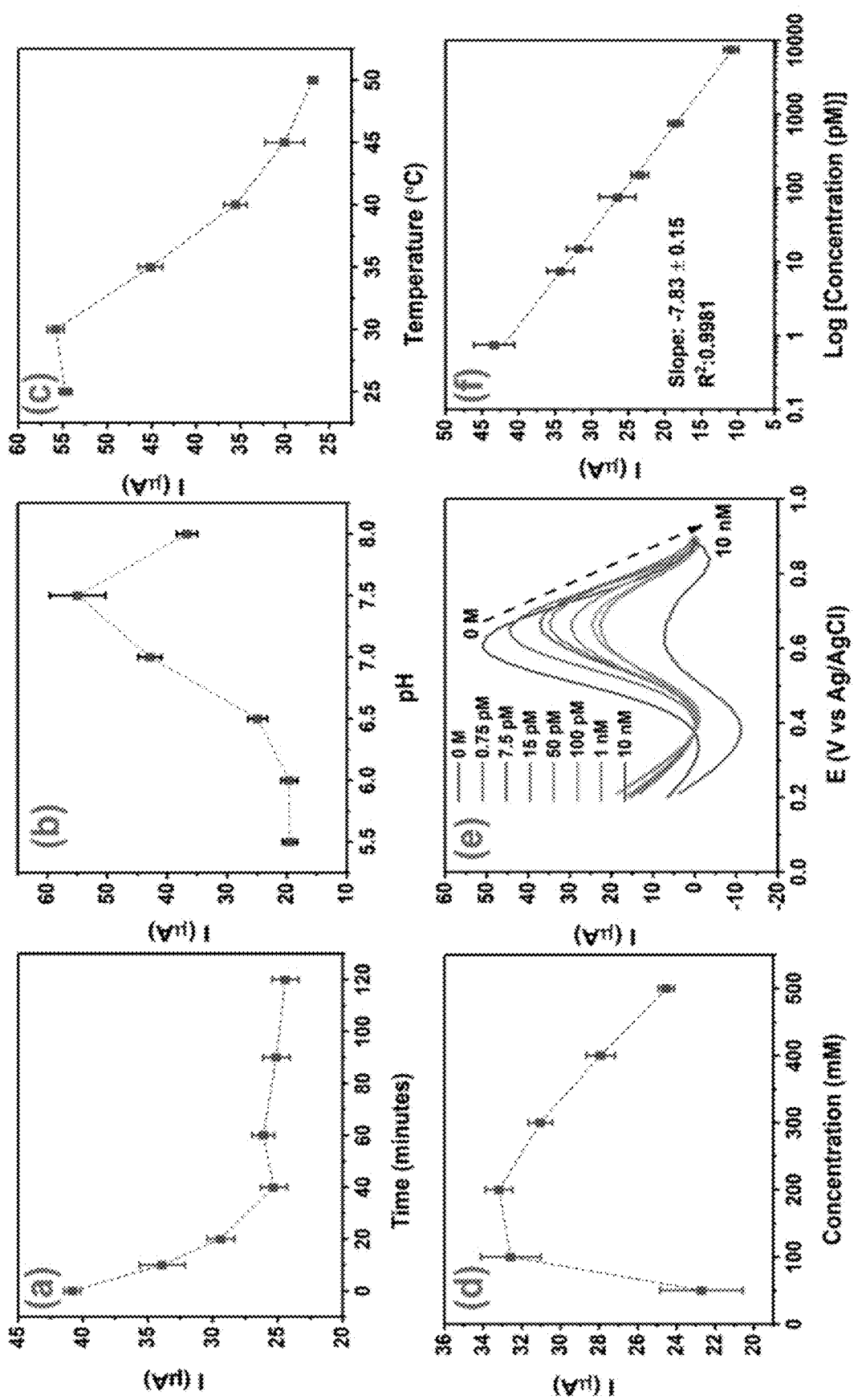
FIG. 5(a) shows a plot of current (in μA) versus time (in minutes (min)) showing peak currents obtained from DPV curves measured in response to 100 pM PDGF-BB for defining the optimum reaction times.
FIG. 5(b) shows a plot of current (in μA) versus pH showing peak currents obtained from DPV curves in response to 100 pM PDGF-BB for analyzing the effect of pH on the peak current.
FIG. 5(c) shows a plot of current (in μA) versus temperature (in °C.) showing peak currents obtained from DPV curves measured in response to 100 pM PDGF-BB for studying the effect of incubation temperature.
FIG. 5(d) shows a plot of current (in μA) versus concentration (in millimolar (mM) showing peak currents obtained from DPV curves measured in response to 100 pM PDGF-BB for studying the effect of KCl concentration on the peak current.
FIG. 5(e) shows a plot of current (in μA) versus voltage (in V versus Ag/AgCl) showing DPV response of the SS/rGO$_{Apt}$ electrode to PDGF-BB ranging from 0 nanomolar (nM) to 10 nM.
FIG. 5(f) shows a plot of current (in μA) versus log [concentration (in pM)] showing the obtained calibration curve of peak currents measured from DPV responses.

Optimum reaction time in aptasensors is referred to as the minimum time required for forming the aptamer-target complex that is both efficient and sufficiently quick. In order to find the optimum reaction time, the SS/rGO$_{Apt}$ samples were incubated with the 100 pM PDGF-BB for different periods ranging from 10 minutes to 120 minutes and analyzed by measuring the peak current of the DPV plot. As shown in FIG. 5(a), the peak current decreases by increasing the incubation time up to 40 minutes and saturates afterward. Therefore, the optimum reaction time was found to be 40 minutes.

The effect of pH on DPV measurement was investigated by conducting DPV measurements on SS/rGO$_{Apt}$ incubated with 100 pM PDGF-BB in the electrolyte of 0.2 M KCl/5 mM K$_3$Fe(CN)$_6$/0.1 M PBS with different pH values in the 5.5-8 range. As shown in FIG. 5(b), the peak response value was recorded at pH of 7.5; thus, the sensing measurements were conducted in the electrolyte with pH of 7.5. The incubation temperature effect on peak current was studied by incubating an SS/rGOApt electrode with 100 pM PDGF-BB at different temperatures ranging from 25° C. to 50° C. The attained results presented in FIG. 5(c) show that the highest peak current was achieved with incubation at 30° C.; hence, the 30° C. was used as the optimum incubation temperature. The result of optimum supporting salt concentration analysis is presented in FIG. 5(d). The highest peak current was recorded in the electrolyte with 200 mM KCl; therefore, 200 mM was chosen as the optimum KCl concentration.

The responses of SS/rGO$_{Apt}$ to 0 nM to 10 nM PDGF-BB measured under optimum conditions are given in FIG. 5(e). The peak current of DPV curves at E≈0.6 V (vs. Ag/AgCl) decreases proportionally to the PDGF-BB concentration increase. The observed trend in peak current results from increased charged transfer resistance due to the isolative properties of PDGF-BB oncoproteins. The calibration curve of peak currents measured from DPV curves is presented in FIG. 5(f). The linear dependence of peak currents to the logarithm of PDGF-BB concentrations has a slop of −7.84 µA log (c$^{-1}$) and the R$^2$ of 0.9981. The correlation of the logarithm of PDGF-BB concentration and SS/rGO$_{Apt}$ peak current can be evaluated as follows (Equation 3), $$i = 41.05 - 7.84 \log(c^{-1}), r = 0.9977 \quad (3)$$

where c is the target concentration (in pM per liter (pM/L)), i is the peak current (in µA), and r is the regression coefficient. Therefore, the sensitivity of SS/rGO$_{Apt}$ to PDGF-BB can be assessed as 7.84 µA log (c$^{-1}$). The LoD for SS/rGO$_{Apt}$ aptasensors based on DPV measurements was estimated as 0.53 pM based on the linear regression (Equation 4), $$LoD = \frac{3S}{b} \quad (4)$$

where S is the standard deviation of the blank response (STDEV=0.2360 µA, n=20), and b is the slope of the calibration curve (b=−1.214 µA c$^{-1}$ (unit of c, pM)) of the DPV peak currents.

The responses of SS/GO$_{Apt}$ to 0 nM-10 nM PDGF-BB measured under optimum conditions reached its saturation point at PDGF-BB concentration of 150 pM. The most probable reason for the narrow range of SS/GO$_{Apt}$ is the low amount of immobilized aptamers due to the limited active area. The sensing analysis of SS/rGO$_{Apt}$ and SS/GO$_{Apt}$ demonstrated that the BPE-graphene deposited on negative feeding electrodes because of its highly porous morphology and higher quality provides more suitable material for biosensing application purposes. Hence, the PET/Au based aptasensors were developed using BPE-rGO.

Example 4—Analysis of PDGF-BB Aptasensor Based on BPE Treated PET/Au Electrodes

Figure 6A:
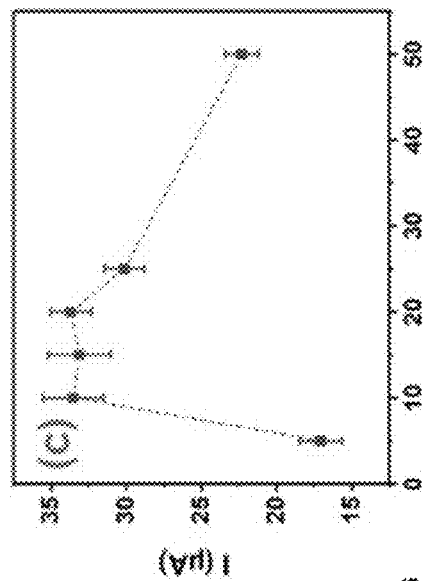
FIG. 6(a) shows a SEM image of BPE-graphene deposited on a PET/Au negative feeding electrode. The scale bar is 1 μm.

The comparative study on BPE-rGO and BPE-GO confirmed that the BPE-rGO provides superior electrode material for envisioned label-free aptasensor. Therefore, the PET/Au electrodes were used as a negative feeding electrode in bipolar exfoliation cell. The SEM analysis, confirmed the successful deposition of BPE-graphene on PET/Au electrodes (FIG. 6(a)). Herein, performance analysis of the aptasensors based on BPE-treaded PET/Au electrodes is given.

Figure 6B:
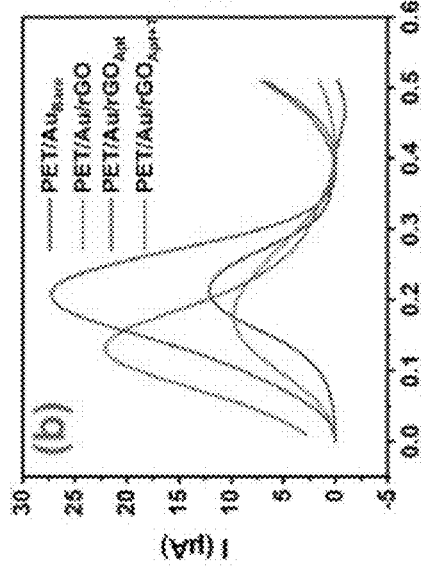
FIG. 6(b) shows a plot of current (in μA) versus voltage (in V versus Ag/AgCl) showing DPV plots of PET/Au-based aptasensors based on graphene deposited on the negative feeding electrode at various development stages and the response of the aptasensor to 100 pM PDGF-BB. The curve with the highest I value at 0.2 V is for PET/Au/rGO$_{Apt}$; the curve with the highest I value at 0.1 V is for PET/Au/rGO; the curve with the lowest I value at 0.1 V is for PET/A$_{uBare}$; and the curve with the second-lowest I value at 0.5 V is for PET/Au/rGO$_{Apt+T}$ (aptamer immobilized and target present).
Figure 6C:
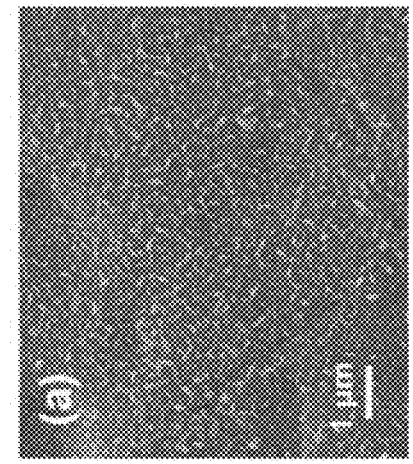
FIG. 6(c) shows a plot of current (in μA) versus concentration (in micromolar (μM)) showing peak currents obtained from DPV curves measured in response to 100 pM PDGF-BB for studying the effect of aptamer concentration.

In FIG. 6(b), DPV plots of aptasensors based on BPE-treaded PET/Au electrodes at different development stages are presented. The DPV results show a similar performance pattern as DPV analysis of SS based electrodes, in which deposition of BPE-rGO has increased the DPV peak current of BPE-treaded PET/Au electrodes (designated as PET/Au/rGO) with a value of 22.2 µA compared to bare PET/Au electrodes (designated as PET/A$_{uBare}$) with peak current value of 12.04 µA. The DPV plot of PET/Au/rGO electrodes after aptamer immobilization (designated as PET/Au/rGO$_{Apt}$) shows an increase in peak current with a value of 27.45 µA, as discussed in Example 2.

The optimum aptamer concentration for PET/Au/rGO-based aptasensors was analyzed by measuring the DVP response of PET/Au/rGO based aptasensor prepared with specific aptamer concentration to 100 pM PDGF-BB. A separate PET/Au/rGO$_{Apt}$ electrode was prepared using an aptamer concentration ranging from 0.5-50 µM. As shown in FIG. 6©, the PET/Au/rGO$_{Apt}$ aptasensor showed its peak DPV response in a sample prepared with an aptamer concentration of 10 μM, and the peak current saturates afterward. Hence, the 10 μM aptamer concentration was utilized for sensing performance analysis.

Figure 6D:
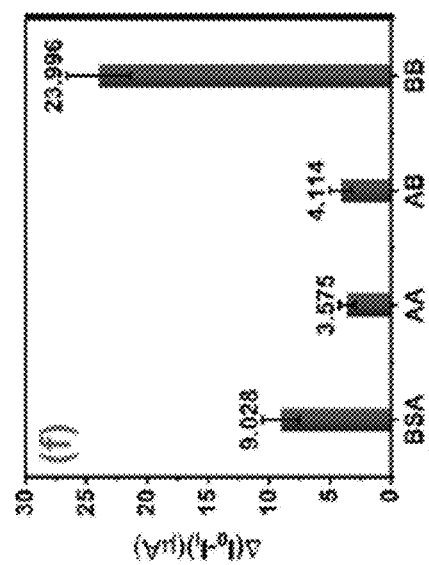
FIG. 6(d) shows a plot of current (in μA) versus voltage (in V versus Ag/AgCl) showing DPV curves of the PET/Au/rGO$_{Apt}$ electrode response to PDGF-BB ranging from 0 M to 20 nM. The higher curves are for lower concentrations, with the exception that the lowest curve at 0.2 V is for 10 nM.
Figure 6E:
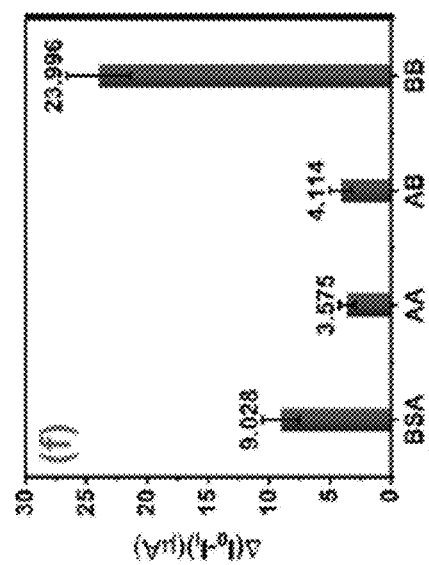
FIG. 6(e) shows a plot of current (in μA) versus log [concentration (in pM)] showing the obtained calibration curve of peak currents measured from DPV responses.
Figure 6F:
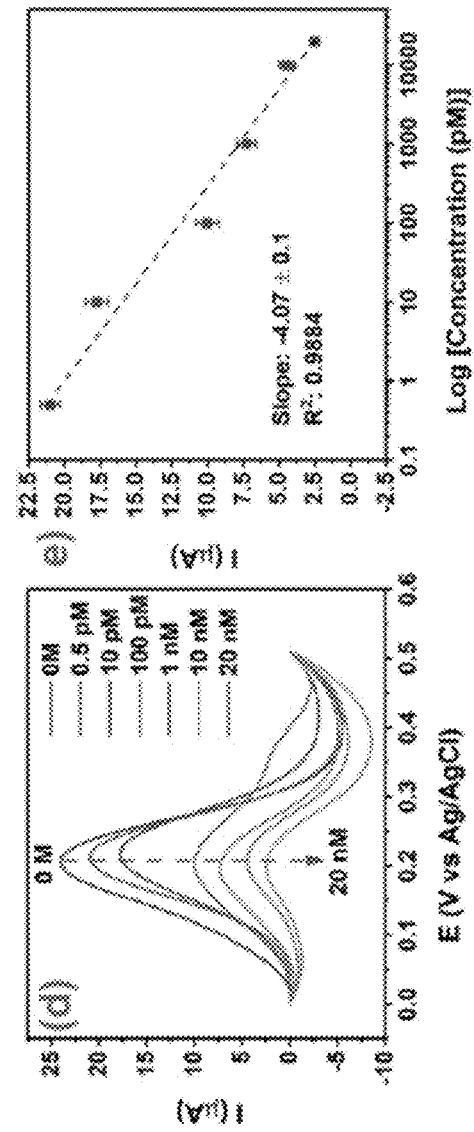
FIG. 6(f) shows a bar chart of $\Delta(I_o-I_t)$ (in μA), showing DPV peak current measured in response of PET/Au/rGO$_{Apt}$ electrodes to 10 nM PDGF-AA, 1 microgram per milliliter (μg/ml) bovine serum albumin (BSA), 10 nM PDGF-AB, and 100 pM PDGF-BB.

The responses of PET/Au/rGO$_{Apt}$ to 0 nM-20 nM PDGF-BB measured under optimum conditions are given in FIG. 6(d). Similar to the sensing performances of aptasensors based on SS electrodes, the peak current of DPV curves decreases proportionally to the increase of PDGF-BB concentration. The calibration curve of peak currents measured from DPV curves is presented in FIG. 6(e). The linear dependence of peak currents to the logarithm of PDGF-BB concentrations has a slop of $-4.07$ μA log $(c^{-1})$ and the $R^2$ of 0.9884. The correlation of PET/Au/rGO$_{Apt}$ peak current to the logarithm of PDGF-BB concentration can be assessed as following (Equation 5), $$i = 20.06 - 4.07 \log(c^{-1}), r=0.9854 \qquad (5)$$

where i is the peak current (μA), c is the PDGF-BB concentration (pM/L), and r is the regression coefficient. Hence, the DPV measurement's sensitivity to PDGF-BB can be calculated as 4.07 μA log $(c^{-1})$. The LoD for PET/Au/rGO$_{Apt}$ aptasensors based on DPV measurements was calculated as 0.65 pM based on the linear regression (Equation 4) in which S was calculated as 0.174 μA (n=10), and b was calculated as 0.81 μA $c^{-1}$.

The selectivity of the PET/Au/rGO$_{Apt}$ electrodes was investigated via recording the response of the aptasensors to 1 microgram per milliliter (μg/mL) bovine serum albumin (BSA), 10 nM of PDGF-BB oncoprotein's isomers (i.e., PDGF-AB and PDGF-AA) along with 100 pM PDGF-BB. The concentrations of interference agents were chosen to be approximately 100 times higher than concentrations of the target molecules. The DPV peak currents measured for selectivity are presented in FIG. 6(f), in which the peak current was measured from the DPV curves and differentiated from the aptasensor's blank response. The DPV peak current of PET/Au/rGO$_{Apt}$ aptasensor to PDGF-BB was 6.71 and 5.83 times higher than that of PDGF-AA aptasensors and PDGF-AB, respectively. The higher response of the PET/Au/rGO$_{Apt}$ aptasensor to BSA than PDGF-AA and PDGF-AB is perhaps due to the bigger size of this protein and higher physical adsorption of BSA on the surface of the PET/Au/rGO$_{Apt}$ aptasensor.

The storage stability of the PET/Au/rGO$_{Apt}$ aptasensor was analyzed by conducting continuous electrochemical measurements on PET/Au/rGO$_{Apt}$ in response to 100 pM PDGF-BB every day. The DPV peak current 25.4 μA of the PET/Au/rGO$_{Apt}$ to 100 pM PDGF-BB after 6 days was 91.02% of the initial capacitive response (23.12 μA), which implies that the envisioned aptasensor has an adequate storage stability.

The table in FIG. 7 summarizes several electrochemical aptasensors, with the electrochemical aptasensor of embodiments of the subject invention being the bottom one in the table (SS and PET/Au electrodes with BPE rGO modification). The electrochemical aptasensor of embodiments of the subject invention exhibited a wide linear range and noticeable improvement compared to label-free PDGF-BB aptasensors based on Au electrodes. It sufficiently covers the healthy levels of PDGF-BB as well as elevated levels in patients with cancer diseases. Compared to other Au-based aptasensors, the PET/Au/rGO$_{Apt}$ showed a noticeable increase in linear range while having low LoD. The attained LoD of detection of 0.65 pM (the equivalent of 1.29 picograms per milliliter (pg/ml)) is adequately lower than the minimum cut-off point of 0.1 nanograms per milliliter (ng/ml) for the healthy levels of PDGF-BB in human serums.

The comparative study on BPE-graphene deposited on negative and positive electrodes confirmed that the BPE-graphene deposited on negative feeding electrode (i.e., rGO) is excellent for biosensing applications. The SEM and TEM analysis revealed that BPE-graphene deposited on the negative feeding electrode was porous graphene with a pore size of 100 nm (or about 100 nm) and most probably comprising single-layer graphene nanosheets. The electrochemical and biosensing performance analysis confirmed that the BPE-rGO provides a more suitable active material for label-free aptasensing than BPE-GO. The exemplary label-free electrochemical PDGF-BB aptasensor based on BPE-rGO showed a noticeably better sensing performance than the similar BPE-GO based aptasensor. Hence, the label-free PDGF-BB aptasensor (which can be disposable) was fabricated using BPE-rGO. The PET/Au/rGO$_{Apt}$ aptasensor showed a wide linear range of 0.0007 nM-20 nM, high sensitivity of 4.07 μA log $(c^{-1})$ (unit of c being pM/L), and a low limit of detection of 0.65 pM (S/N=3). This aptasensor demonstrated that electrochemical bipolar exfoliation of graphene is an excellent technique for developing feasible, cheap, and reliable biosensors.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A biosensor for detecting a biomarker, the biosensor comprising:
    an electrode comprising a metal;
    reduced graphene oxide (rGO) disposed on the electrode, the rGO comprising graphene nanosheets; and
    a plurality of aptamers disposed on the rGO, the plurality of aptamers being configured to bind to the biomarker,
    the plurality of aptamers being directly immobilized on the graphene nanosheets without any mediator or linking layer disposed therebetween,
    the rGO covering at least 90% of an upper surface of the metal of the electrode, and
    the rGO having a vertically aligned structure.

2. The biosensor according to claim 1, the electrode further comprising a substrate on which the metal is disposed.

3. The biosensor according to claim 2, the substrate being a polymer.

4. The biosensor according to claim 3, the substrate being polyethylene terephthalate (PET).

5. The biosensor according to claim 1, the metal being gold (Au).

6. The biosensor according to claim 1, the metal being stainless steel (SS).

7. The biosensor according to claim 1, the biomarker being a cancer biomarker.

8. The biosensor according to claim 1, the biomarker being platelet-derived growth factor-BB (PDGF-BB).

9. The biosensor according to claim 1, the biosensor being label-free.

10. The biosensor according to claim 1, the biosensor being disposable.

11. The biosensor according to claim 1, the biosensor having a lower limit of detection for the biomarker of less than 1 picomolar (pM).

12. A biosensor for detecting a biomarker, the biosensor comprising:
an electrode comprising a metal;
reduced graphene oxide (rGO) disposed on the electrode, the rGO comprising graphene nanosheets; and
a plurality of aptamers disposed on the rGO, the plurality of aptamers being configured to bind to the biomarker,
the biomarker being platelet-derived growth factor-BB (PDGF-BB),
the rGO covering at least 90% of an upper surface of the metal of the electrode,
the rGO having a vertically aligned structure,
the biosensor being label-free,
the biosensor being disposable,
the biosensor having a lower limit of detection for the biomarker of less than 1 picomolar (pM),
the plurality of aptamers being directly immobilized on the graphene nanosheets without any mediator or linking layer disposed therebetween, and
the electrode comprising either feature a) or feature b):
 a) the electrode comprising a substrate on which the metal is disposed, the metal being gold (Au), and the substrate being polyethylene terephthalate (PET); or
 b) the metal of the electrode being stainless steel (SS).

\* \* \* \* \*